(12) United States Patent
Kaslow

(10) Patent No.: US 7,341,733 B2
(45) Date of Patent: *Mar. 11, 2008

(54) COMPOSITIONS EXHIBITING ADP-RIBOSYLTRANSFERASE ACTIVITY AND METHODS FOR THE PREPARATION AND USE THEREOF

(76) Inventor: Harvey R. Kaslow, 2430 Kenilworth Ave., Los Angeles, CA (US) 90039

(*) Notice: Subject to any disclaimer, the term of this patent is extended or adjusted under 35 U.S.C. 154(b) by 743 days.

This patent is subject to a terminal disclaimer.

(21) Appl. No.: 10/314,192

(22) Filed: Dec. 6, 2002

(65) Prior Publication Data

US 2003/0113311 A1 Jun. 19, 2003

Related U.S. Application Data

(60) Continuation of application No. 09/510,664, filed on Feb. 22, 2000, now Pat. No. 6,514,499, which is a division of application No. 08/482,758, filed on Jun. 7, 1995, now Pat. No. 6,056,960.

(51) Int. Cl.
*A61K 45/00* (2006.01)
(52) U.S. Cl. ................... 424/278.1; 424/282.2
(58) Field of Classification Search ............... None
See application file for complete search history.

(56) References Cited

OTHER PUBLICATIONS

Stedman's Medical Dictionary, (on-line version) 2000, lines 1-3.*
Abstract of Wheeler (Salud p'ublica de M'exico, (Jul.-Aug. 1997) 39 (4) 283-7).*
Efferson et al (Anticancer research, 2005, vol. 25, pp. 715-724).*
Bachman et al (Journal of Immunology, 2005, vol. 175, pp. 4677-4685).*
Paul, Fundamental Immunology, (text), 1993, p. 1163, second column, first sentence under the heading "Factors Limiting Effective Tumor Immunity" and Table 4).*
Abstract of Semino et al (Journal of Biological Regulators and Homeostatic Agents, 1993, vol. 7, pp. 99-105.*
Abstract of Algarra et al International Journal of Clinical and Laboratory Research, 1997, vol. 27, pp. 95-102).*
Bodey et al (Anticancer Research, Jul.-Aug. 2000, vol. 20, pp. 2665-2676).*
Abstract of Munoz and Peacock (Microbiology and Immunology, 1989, vol. 33, No. 4, pp. 341-355).*
Munoz and Peacock (Microbiology and Immunology, 1989, vol. 33, No. 4, pp. 341-355).*

* cited by examiner

*Primary Examiner*—Karen A. Canella
(74) *Attorney, Agent, or Firm*—Berliner & Associates

(57) ABSTRACT

Compositions characterized by ADP-ribosyltransferase activity are useful in promoting prophylactic and/or therapeutic responses as are promoted by, e.g., pertussis toxin but directed against another target antigen (e.g., a cancer-related antigen) in a mammalian patient.

7 Claims, 4 Drawing Sheets

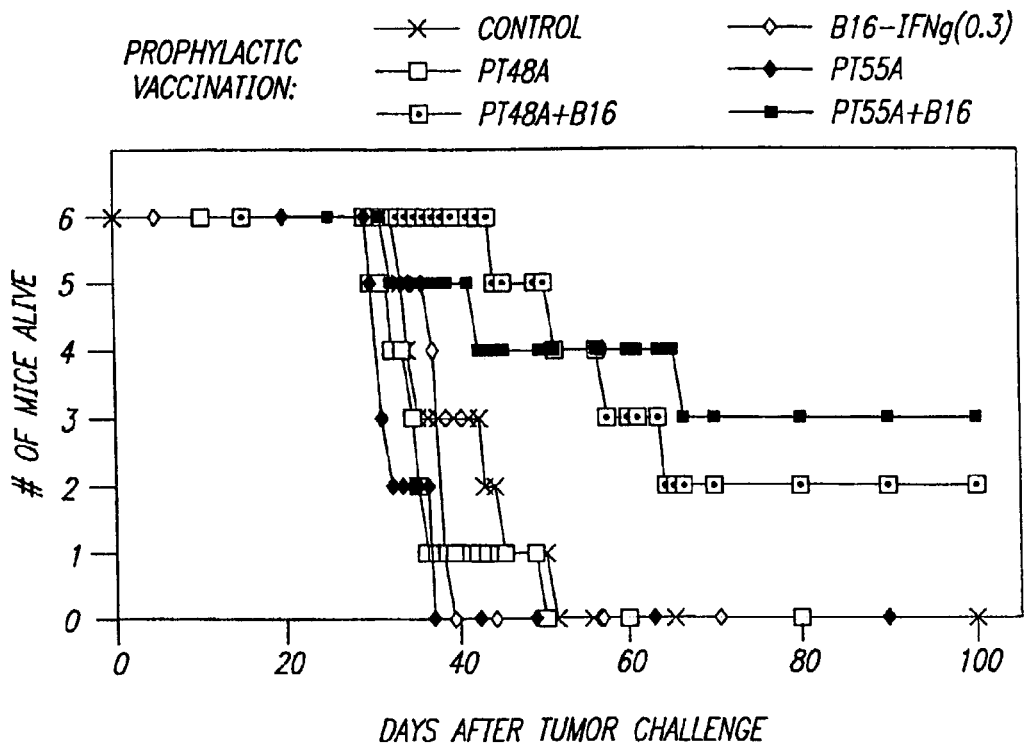
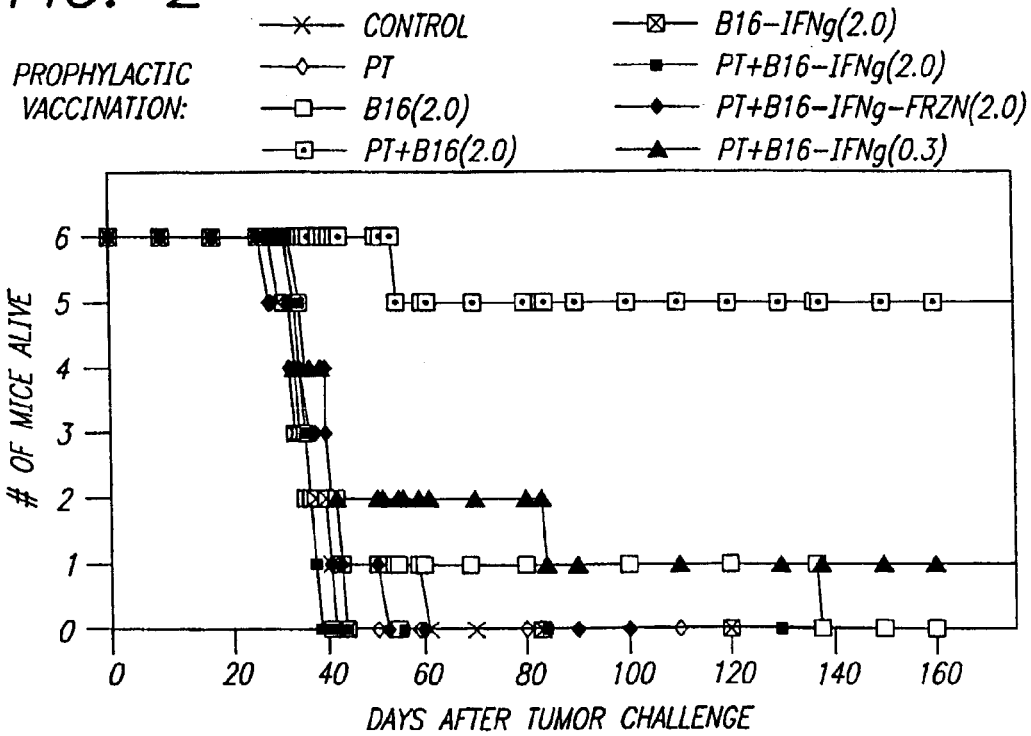

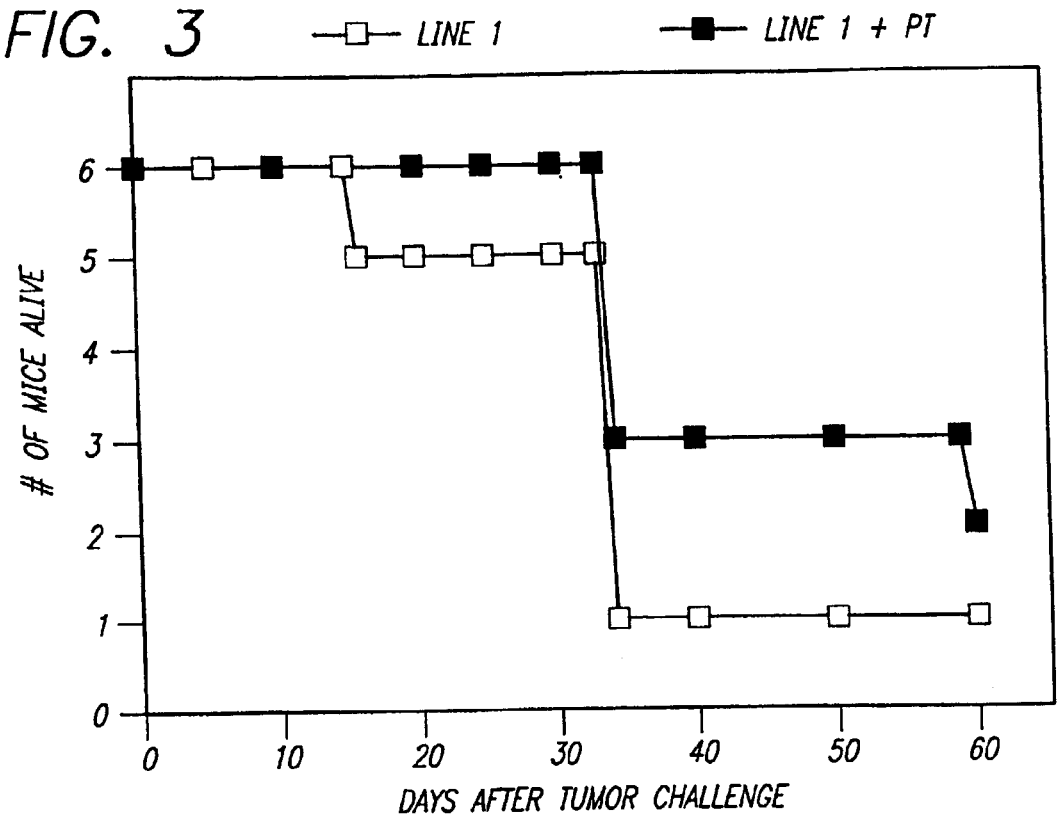
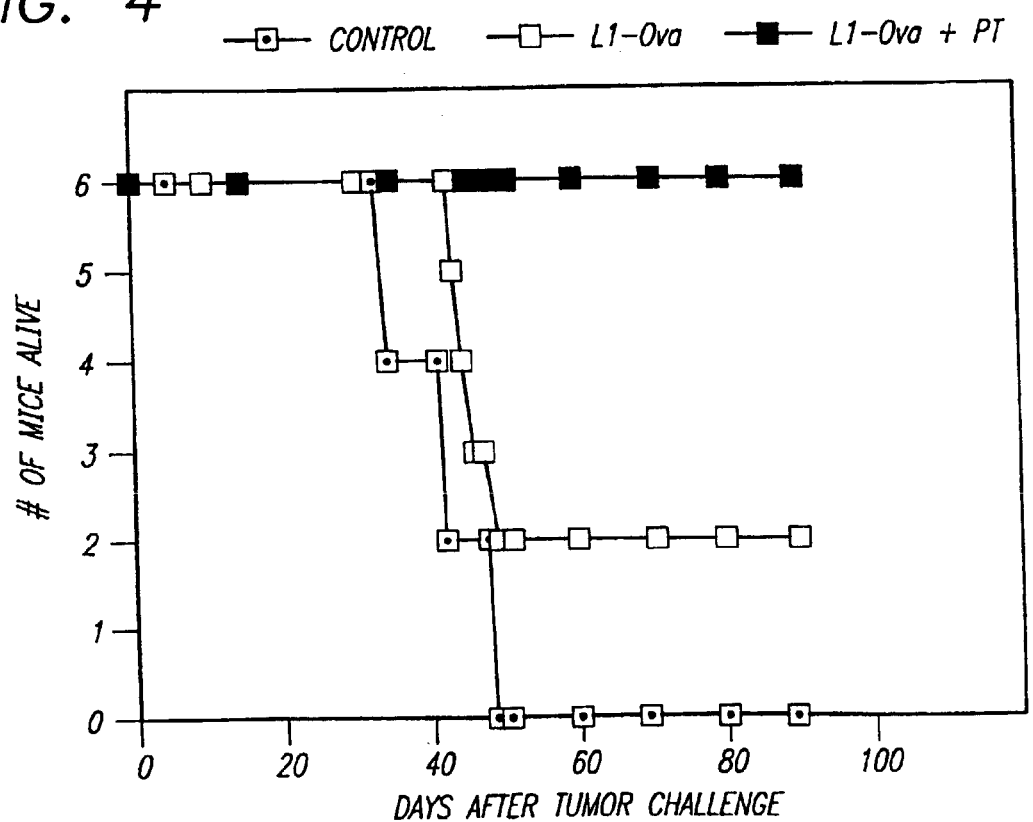

COMPOSITIONS EXHIBITING ADP-RIBOSYLTRANSFERASE ACTIVITY AND METHODS FOR THE PREPARATION AND USE THEREOF

CROSS-REFERENCE WITH RELATED APPLICATIONS

The present application is a continuation of U.S. patent application Ser. No. 09/510,664, filed Feb. 22, 2000, now U.S. Pat. No. 6,514,499 which is a divisional of U.S. patent application Ser. No. 08/482,758, now U.S. Pat. No. 6,056,960, filed Jun. 7, 1995.

BACKGROUND OF THE INVENTION

The present invention relates generally to the fields of medicine and biology. In particular, the present invention is directed towards compositions exhibiting ADP-ribosyltransferase activity which have prophylactic and/or therapeutic activity (e.g., in preventing cancer metastasis, preventing recurrence or reducing the incidence of cancers), as well as methods for the preparation and use thereof.

The use of surgery and radio- or chemotherapy to treat cancer involves the risk of serious side-effects and even death, yet frequently fails to produce substantive benefit. It is not surprising that these methods are rarely used to prevent cancer. It is clear there is a need for better methods to prevent or cure cancer and/or ameliorate the symptoms thereof in a patient.

Immune responses can effectively kill cells that display antigens that mark cells as harboring a pathogen. Vaccines containing such antigens can stimulate these desired responses and protect against disease with little risk. Coupling this experience with the hypothesis that malignant cells may also present a similar marker has led many investigators to search for vaccines that could prevent or cure various types of cancer [McCall, C. A., Wiemer, L., Baldwin, S., & Pearson, F. C. (1989) *Bio/technology* 7, 231-240; Rosenburg, S. A. (1992) *J. Clin. Oncol.* 10, 180-199; Prehn, R. T. (1993) *Proc. Natl. Acad. Sci. U.S.A.* 90, 4332-4333]. The successful development of such a vaccine would involve identifying preparations containing tumor-associated antigens, and learning how to prompt the immune system to properly and specifically kill cells displaying those antigens.

Some vaccines have been spectacularly successful at preventing infectious disease (e.g., smallpox); attempts to make other vaccines have, to date, failed (e.g., AIDS). At times, the lack of success may arise from a failure to elicit a proper response to an antigen, not the unavailability of a suitable antigen. These failures suggest that methods that control immune responses to antigens could greatly benefit the performance of vaccines designed to prevent, treat and/or cure infectious disease.

Similar issues face the development of cancer vaccines. For example, injecting irradiated tumor cells frequently fails to elicit an effective anti-tumor response. However, injecting irradiated tumor cells previously transfected with genes causing production of lymphokines (e.g., GM-CSF) [Dranoff, G., Jaffee, E., Lazenby, A., Golumbeck, P., Levitsky, H., Brose, K., Jackson, V., Hamada, H., Pardoll, D., & Mulligan, R. C. (1993) *Proc. Natl. Acad. Sci. U.S.A.* 90, 3539-3543] can promote anti-tumor responses. Similar results have been obtained with tumor cells transfected to produce foreign major histocompatibility complexes [Plautz, G. E., Yang, Z. Y., Wu, B. Y., Gao, X., Huang, L., & Nabel, G. (1993) *Proc. Natl. Acad. Sci. U.S.A.* 90, 4645-4649], or adhesins, such as B7, normally found on the surface of antigen-presenting cells [Chen, L., Ashe, S., Brady, W. A., Hellstroem, I., Hellstroem, K. E., Ledbetter, J. A., McGowan, P., & Linsley, P. S. (1992) *Cell* 71, 1093-1102; Schwarz, R. H. (1992) *Cell* 71, 1068-1068; Baskar, S., Ostrand-Rosenburg, S., Nabavi, N., Nadler, L. M., Freeman, G. J., & Glimcher, L. H. (1993) *Proc. Natl. Acad. Sci. U.S.A.* 90, 5687-5690; Townsend, S. E., & Allison, J. P. (1993) *Science*. 259, 368-370]. Yet another approach has been to stimulate the immune system with bacteria or factors derived therefrom [McCall et al., 1989, supra].

Pertussis toxin is a protein released from the bacterium *Bordetella pertussis*. The administration of pertussis toxin along with a proper antigen markedly enhances antigen-specific autoimmune disease [Munoz, J. J. (1988) in *Pathogenesis and Immunity in Pertussis* (Wardlaw, A. C., & Parton, R., Eds.) Chapter 8, pp. 173-192, John Wiley & Sons Ltd., New York; Kamradt, T., Soloway, P. D., Perkins, D. L., & Gefter, M. L. (1991) *J. Immunol.* 147, 3296-3302] and antigen-specific delayed-type hypersensitivity reactions, but not antigen-independent inflammatory responses [Sewell, W. A., Munoz, J. J., & Vadas, M. A. (1983) *J. Exp. Med.* 157, 2087-2096; Sewell, W. A., Munoz, J. J., Scollay, R., & Vadas, M. A. (1984) *J. Immunol.* 133, 1716-1722]. There are reports [Likhite, V. V. (1983) U.S. Pat. No. 4,372,945; Minagawa, H., Kakamu, Y., Yoshida, H., Tomita, F., Oshima, H., & Mizuno, D. I. (1988) *Jpn. J. Cancer Res.* 79, 384-389; Minagawa, H., Kobayashi, H., Yoshida, H., Teranishi, M., Morikawa, A., Abe, S., Oshima, H., & Mizuno, D. I. (1990) *Br. J. Cancer* 62, 372-375] that crude preparations of *B. pertussis* can cause anti-tumor responses; the factor in these preparations causing this effect was not identified. Others have shown that lipopolysaccharides from *B. pertussis* can stimulate anti-tumor responses [Ohnishi, M., Kimura, S., Yamazaki, M., Abe, S., & Yamaguchi, H. (1994) *Microbiol. Immunol.* 38, 733-739; Ohnishi.M, Kimura, S., Yamazaki, M., Oshima, H., Mizuno, D.-I., Abe, S., & Yamaguchi, H. (1994) *Br. J. Cancer* 69, 1038-1042].

It is an object of the present invention to provide compositions and methods which do not suffer from the drawbacks attendant to the heretofore-available compositions and methods. In particular, it is an object of the present invention to provide compositions which increase the efficacy of other compositions and methods.

SUMMARY OF THE INVENTION

In accordance with the present invention, there are provided compositions characterized by ADP-ribosyltransferase activity. These compositions are useful in promoting prophylactic and/or therapeutic responses as are promoted by, e.g., pertussis toxin but directed against another target antigen (e.g., a cancer-related antigen) in a mammalian patient.

BRIEF DESCRIPTION OF THE DRAWINGS

The invention may be better understood with reference to the accompanying drawings, in which:

FIG. 1 illustrates the protection against B16 melanoma afforded by vaccination of C57/BL mice with irradiated B16 tumor cells with or without coadministration of pertussis toxin (PT lots 48A and 55A);

FIG. 2 illustrates the protection against B16 melanoma afforded by vaccination of C57/BL mice with irradiated B16 melanoma cells first incubated either with or without interferon-gamma (IFNg) and injected either with or without coadministration of pertussis toxin (PT);

FIG. 3 illustrates the protection against line 1 carcinoma afforded by vaccination of BALB/C mice with irradiated line 1 cells with or without coadministration of PT:

FIG. 4 illustrates the protection against line 1 carcinoma transfected to produce ovalbumin (L1-Ova) afforded by vaccination of BALB/C mice with irradiated L1-Ova cells with or without coadministration of PT;

DETAILED DESCRIPTION OF PREFERRED EMBODIMENTS

Figure 5:
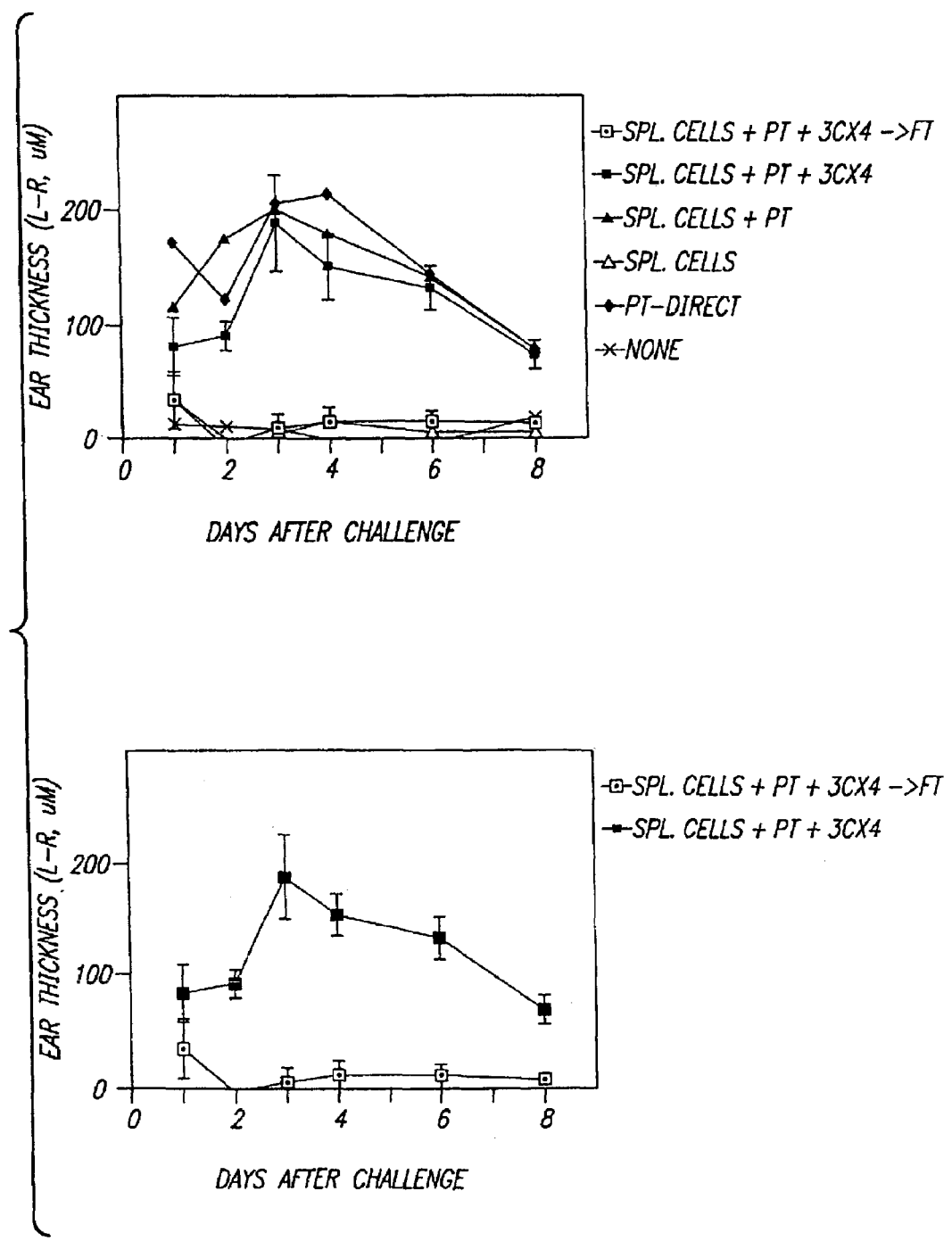
FIG. 5 illustrates the ear-swelling response to irradiated L1-Ova cells of BALB/C mice previously vaccinated with irradiated carcinoma cells with or without coadministration of PT, or spleen cells incubated either with or without pertussis toxin and then mixed with the anti-pertussis toxin monoclonal antibody 3CX4.

Pursuant to the present invention, responses as are promoted by pertussis toxin are directed against one or more target antigens by administration to a mammalian patient of an effective amount of a composition in accordance with the present invention characterized by ADP-ribosyltransferase activity. Pertussis toxin is shown herein to increase the efficacy of cancer vaccines. Compositions in accordance with the present invention characterized by ADP-ribosyltransferase activity also potentiate the activity of other vaccines and other types of therapeutic agents.

Pertussis toxin is a multi-subunit protein comprised of an A protomer consisting of a single catalytic S1 subunit, and a B oligomer containing one S2, one S3, two S4, and one S5 subunits. The B oligomer binds the toxin to specific receptors on target cells, thus delivering the S1 subunit to the cell membrane where, after it is activated, it catalyzes the transfer of ADP-ribose from NAD to a specific cysteine residue in specific acceptor proteins, typically the alpha subunit of regulatory proteins, termed G-proteins, that bind guanine nucleotides [Ui, M. (1990) in *ADP-Ribosylating Toxins and G Proteins* (Moss, J., & Vaughan, M., Eds.) Chapter 4, pp. 45-77, American Society for Microbiology, Washington, D.C.].

Although there are many other bacterial toxins known to catalyze ADP-ribosylations, to my knowledge there are no reports of other bacterial toxins catalyzing the specific ADP-ribosylation reactions catalyzed by pertussis toxin [Moss, J., & Vaughan, M., Eds. (1990) *ADP-ribosylating Toxins and G Proteins*, American Society for Microbiology, Washington, D.C.]. Although a eukaryotic ADP-ribosyltransferase activity has been described that adds ADP-ribose to cysteine residues, and perhaps to the same protein or residue as does pertussis toxin, its functional significance appears to be unknown [Williamson, K. C., & Moss, J. (1990) in *ADP-Ribosylating Toxins and G Proteins* (Moss, J., & Vaughan, M., Eds.) pp. 493-510, American Society for Microbiology, Washington, D.C.]. If such an enzyme could be manipulated to catalyze the same reaction as does pertussis toxin, then it could become a functional analog of the toxin.

Other defined agents currently used to boost anti-tumor responses do not appear to contain the ADP-ribosyltransferase activity of pertussis toxin. In experiments involving stimulation of delayed-type hypersensitivity (DTH) or autoimmune responses, pertussis toxin is commonly used in addition to other adjuvants, such as complete Freund's adjuvant or superantigens [Munoz, J. J., & Sewell, W. A. (1984) *Infect. Immun.* 44, 637-641; Sewell, W. A., de Moerloose, P. A., McKimm-Breschkin, J. L., & Vadas, M. A. (1986) *Cell. Immunol.* 97, 238-247; Kamradt et al., 1991, supra]; thus, the mechanism underlying pertussis toxin action and these other adjuvants is different.

It is presently preferred to administer to mice an amount of the exemplary active agent sufficient to cause lymphocytosis, which serves as a positive control to demonstrate that the agent is active in vivo. Lymphocytosis may not be required for the beneficial effects, and amounts less than this amount may be sufficient for other responses [Munoz, J. J., Arai, H., Bergman, R. K., & Sadowski, P. L. (1981) *Infect. Immun.* 33, 820-826], including the anti-tumor response, particularly if the agent is directed towards specific cellular targets. In humans, another measure of pertussis toxin action may be more appropriate, for example enhanced insulin secretion or glucose clearance. A single intravenous injection of 0.5 or 1.0 ug pertussis toxin protein per kg body weight has been found to promote insulin secretion in healthy, control humans with no clearly-evident toxic or adverse response. [Toyota, T., Kai, Y., Kakizaki, M., Sakai, A., Goto, Y., Yajima, M., & Ui, M. (1980) *Tohoku J. Exp. Med.* 130, 105-116]. The agent may be administered by a variety of appropriate routes (e.g. intravenously, intraperitoneally) as long as the agent reaches cells which, upon intoxication, provide an anti-tumor response.

In the examples given herein, the effective dose of pertussis toxin injected intraperitoneally into mice appears to be less than 400 ng per mouse (typical weight of 25 gm) As would readily be appreciated by those skilled in the field, an optimum dose of active agent for any given mammalian patient may be determined empirically.

Properly administered, the effective dose for purposes of the present invention could be no more than or even less than the amount of activity contained in whole-cell pertussis vaccines. Such vaccines have been shown to reduce hyperglycemia in diabetics requiring high dosage of insulin [Dhar, H. L., Dhirwani, M. K., & Sheth, U. K. (1975) *Brit. J. Clin. Pract.* 29, 119-120], perhaps by increasing secretion of insulin. Although it has been claimed that an untoward event can arise from about 300,000 doses of this vaccine, many doubt that these rare events are causally related to the vaccine, or the pertussis toxin it contains. Millions of infants are still routinely immunized with such vaccines in the United States [Cherry, J. D., Brunell, P. A., Golden, G. S., & Karzon, D. T. (1988) *Pediatrics*. 81(6 Part 2), 939-984]. Thus the risks from suitable agents should be well accepted by, e.g., cancer victims facing extended periods of suffering and death.

Just as intoxication of some cells by pertussis toxin can promote anti-tumor responses, intoxication of other cells could diminish the desired response, or cause unwanted side-effects. Thus, identifying the target(s) of pertussis toxin sufficient to promote desired anti-tumor responses leads to preferred compositions and methods contemplated as within the scope of the present invention which more fully exploit the activity of the compositions of the present invention.

Much is known concerning the structure and function of pertussis toxin; this knowledge has arisen, in large part, from efforts to better use pertussis toxin in pertussis vaccines [Sato, H., & Sato, Y. (1984) *Infect. Immun.* 46, 415-421; Pizza, M., Covacci, A., Bartoloni, A., Perugini, M., Nencioni, L., De-Magistris, M. T., Villa, L., Nucci, D., Manetti, R., Bugnoli, M., Giovannoni, F., Olivieri, R., Barbieri, J. T., Sato, H., & Rappuoli, R. (1989) *Science.* 246, 497-500; Loosmore, S. M., Zealey, G. R., Boux, H. A., Cockle, S. A., Radika, K., Fahim, R. E. F., Zobrist, G. J., Yacoob, R. K., Chong, P. C.-S., Yao, F.-L., & Klein, M. H. (1990) *Infect. Immun.* 58, 3653-3662; Nencioni, L., Pizza, M., Bugnoli, M., De-Magistris, T., Di-Tommaso, A., Giovannoni, F., Manetti, R., Marsili, I., Matteucci, G., Nucci, D., Olivieri, R., Pileri, P., Presentini, R., Villa, L., Kreeftenberg, J. G., Silvestri, S., Tagliabue, A., & Rappuoli, R. (1990) *Infect. Immun.* 58, 1308-1315; Burnette, W. N. (1991) in *Vaccine Research: A Series of Advances*, Vol. 1 (Koff, W., & Six, H. R., Eds.) Chapter 6, pp. 143-193, Marcel Dekker, Inc., New York] and to study transmembrane signaling [Ui, 1990, supra]. Knowledge of site(s) of action of pertussis toxin which enhance anti-tumor effects leads to strategies to identify therapeutic targets of pertussis toxin and improve its efficacy.

For example, cells involved in the immune response (e.g. antigen-presenting or antigen-recognizing cells) are plausible targets. Such cells can be incubated and intoxicated with pertussis toxin ex vivo, the remaining toxin neutralized with monoclonal antibodies, and the intoxicated cells placed back in vivo.

Mutations in the B oligomer could be used to target pertussis toxin to sufficient targets. For example, the B oligomer contains multiple binding sites with differing specificities. Two of these sites have been identified, one in subunit S2, the other in subunit S3. The site in S2 appears to cause the toxin to bind to lung cilia; the site in S3 appears to cause binding to macrophages. Macrophages can contribute to immune responses. In addition, mutations in S2 and S3 can convert the binding properties of one to the other [Saukkonen, K., Burnette, W. N., Mar, V. L., Masure, H. R., & Tuomanen, E. I. (1992) *Proc. Natl. Acad. Sci. U.S.A.* 89, 118-122]. Such mutations could limit the binding of pertussis toxin to one or the other cell type. Such mutations could be used to direct pertussis toxin away from cells which, when intoxicated, produce an undesired response, and towards cells that, when intoxicated, produce a desired response. Other alterations of pertussis toxin structure which alter its binding properties may provide analogs with greater efficacy and/or diminished undesired side-effects. Alternatively, antibodies or cytokines (e.g. interleukin-2) could be adsorbed, coupled covalently, or expressed as fusion-proteins with pertussis toxin or analogs containing its ADP-ribosyltransferase activity to deliver this activity with greater specificity than does the naturally-occurring B oligomer.

DNA encoding for the activity of pertussis toxin could be delivered to specific cell types. The portions of the toxin sequence required for its ADP-ribosyltransferase and other functions is being revealed by computer [Domenighini, M., Montecucco, C., Ripka, W. C., & Rappuoli, R. (1991) *Molec. Microbiol.* 5, 23-31], enzymatic [Krueger & Barbieri, 1994], and x-ray crystal studies of its structure [Stein, P. E., Boodhoo, A., Armstrong, G. D., Cockle, S. A., Klein, M. H., & Read, R. J. (1994a) *Structure* 2, 45-57; Stein, P. E., Boodhoo, A., Armstrong, G. D., Heerze, L. D., Cockle, S. A., Klein, M. H., & Read, R. J. (1994b) *Struct. Biol.* 1, 591-596]. The DNA sequence of the pertussis toxin gene from *Bordetella pertussis* has been reported [Nicosia, A., Perugini, M., Franzini, C., Casagli, M. C., Borri, M. G., Antoni, G., Almoni, M., Neri, P., Ratti, G., & Rappuoli, R. (1986) *Proc. Natl. Acad. Sci. U.S.A.* 83, 4631-4635].

Because pertussis toxin may be causing coordinated changes in the activities of several types of cells involved in immune responses, the compositions and methods of the present invention may profitably be employed in combination with other approaches. For example, cyclic-AMP is thought to increase B7 expression on antigen-presenting cells [Nabavi, N., Freeman, G. J., Gault, A., Godfrey, D., Nadler, L. M., & Glimcher, L. H. (1992) *Nature* 360, 266-268], and expression of B7 may promote anti-tumor responses [Chen, S.-H., Li Chen, X. H., Wang, Y., Kosai, K.-I., Finegold, M. J., Rich, S. S., & Woo, S. L. C. (1995) *Proc. Natl. Acad. Sci. U.S.A.* 92, 2577-2581; Schwarz, 1992, supra; Baskar et al., 1993, supra; Townsend & Allison, 1993, supra]. Pertussis toxin can increase cyclic-AMP, and thus may increase B7 expression. As increasing cyclic-AMP in an antigen-presenting cell likely does more than increase expression of B7, pertussis toxin may cause antigen-presenting cells to activate T cells in ways that would benefit approaches based on increasing the expression of B7.

Pertussis toxin may act at sites of antigenic stimulation by either promoting the release of stimulatory lymphokines (e.g., interferon-gamma) [Sewell et al., 1986, supra] or reducing the effects of inhibitory factors. Therefore, the administration of pertussis toxin might improve the effectiveness of smaller doses of lymphokines used to promote anti-tumor responses. If so, then, properly used, pertussis toxin might reduce dangerous side-effects associated with the use of such lymphokines. Further, the toxin might improve the action of other adjuvants that act by causing the release of lymphokines.

The mechanisms by which pertussis toxin promotes effectiveness of tumor vaccines might also enhance the efficacy of vaccines against cells harboring pathogens such as parasites, bacteria, or viruses. In addition, the G-proteins modified by pertussis toxin mediate the actions of a wide variety of extracellular effectors in many tissues [Furman, B. L., Sidey, F. M., & Smith, M. (1988) in *Pathogenesis and Immunity in Pertussis* (Wardlaw, A. C., & Parton, R., Eds.) Chapter 7, pp. 147-172, John Wiley & Sons, New York; Bourne, H. R., Sanders, D. A., & McCormick, F. (1990) *Nature* 348, 125-132]. Thus, compositions exhibiting ADP-ribosyltransferase activity may have therapeutic value in other systems (e.g. diabetes) [Dhar et al., 1975, supra; Toyota et al., 1980, supra].

There is evidence that anti-IL4 antibodies enhance the promotion of DTH by pertussis toxin [Mu, H.-H., & Sewell, W. A. (1994) *Immunology* 83, 639-645; Rosoff, P. M., Walker, R., & Winberry, L. (1987) *J. Immunol.* 139, 2419-2423]. Thus, antagonists of IL4 may help promote the anti-tumor effect of compositions in accordance with the present invention. As more is learned about the types of immune responses that kill tumor cells, the information will suggest other potentially beneficial combinations of other agents and the materials and methods of this invention.

The antigen may be added to the composition, or it may be found in tumor cells already in vivo. For example, tumor cells in vivo could be irradiated or treated with interferon-gamma with the simultaneous administration of PT. Alternatively, methods introducing new genes into tumor cells in vivo may render them more immunogenic [Chen, S.-H. et al., 1995, supra; Sun, W. H., Burkholder, J. K., Sun, J., Culp, J., Turner, J., Lu, X. G., Pugh, T. D., Ershler, W. B., & Yang, N.-S. (1995) *Proc. Natl. Acad. Sci. U.S.A.* 92, 2889-2893].

In all of these cases, pertussis toxin activity could then be used to promote an anti-tumor response against the in vivo cells.

In Example 1, a recombinant analog of pertussis toxin was used which lacks ADP-ribosyltransferase activity, but retains a general structure equivalent to naturally-occurring pertussis toxin as evidenced by the ability to agglutinate erythrocytes (indicating that the B oligomer is functionally intact) and to elicit antibodies that neutralize naturally-occurring pertussis toxin [Nencioni et al., 1990, supra]. The result in the example demonstrates that the ADP-ribosyltransferase activity of pertussis toxin is required for the anti-tumor effect, but does not rule out a role for other activities of the toxin. For example, the B oligomer not only delivers the S1 subunit containing ADP-ribosyltransferase activity to cells, but also can produce biological effects [Tamura, M., Nogimori, K., Yajima, M., Ase, K., & Ui, M. (1983) *J. Biol. Chem.* 258, 6756-6761; Rosoffet al., 1987, supra; Strnad, C. F., & Carchman, R. A. (1987) *FEBS. Lett.* 225, 16-20; Stewart, S. J., Prpic, V., Johns, J. A., Powers, F. S., Graber, S. E., Forbes, J. T., & Exton, J. H. (1989) *J. Clin. Invest.* 83, 234-242].

To demonstrate that the anti-tumor effects of pertussis toxin are not restricted to one tumor type or strain of mouse, Examples 1-3, and 8 demonstrate an effect against B16 melanoma in C57BL/6 mice, and Examples 4, 5, and 7 demonstrate an effect against a lung carcinoma termed line 1, syngeneic to Balb/c mice [Blieden, T. M., McAdam, A. J., Foresman, M. D., Cerosaletti, K. M., Frelinger, J. G., & Lord, E. M. (1991) *Int. J. Cancer Supplement*, vol 6, 82-89]. The results with the lung carcinoma suggests that the effect of pertussis toxin is increased if the tumor is made more immunogenic by the expression of a foreign protein, in this case chicken ovalbumin.

Examples 6-8 also demonstrate that the immune system is a sufficient target of the toxin. The approach used was to take spleen cells from one mouse, incubate them overnight with or without pertussis toxin, and then co-administer the spleen cells with irradiated tumor cells into a syngeneic mouse, which was then subsequently challenged with live tumor cells. A problem that can be encountered with this approach is that pertussis toxin reversibly binds to the surface of the spleen cells. Thus, when cells incubated with pertussis toxin are injected into a mouse, the toxin can be transferred from the injected cells to cells of the recipient mouse. This process must be blocked in order to establish that the cultured cells are in fact a sufficient target of the toxin. A monoclonal antibody, termed 3CX4 [Kenimer, J. G., Kim, K. J., Probst, P. G., Manclark, C. R., Burstyn, D. G., & Cowell, J. L. (1989) *Hybridoma.* 8, 37-51], was therefore used to block transfer of the toxin to the recipient mouse.

To test the ability of the antibody to block transfer, the experiment reported in Example 6 was performed. Spleen cells were incubated overnight either with or without pertussis toxin, washed, and mixed with 3CX4. Irradiated tumor cells were then injected into mice either with or without co-administration of these cells. For some mice, the toxin-treated cells were lysed by freeze-thawing prior to injection; pertussis toxin tolerates freeze-thawing [Kaslow, H. R., & Burns, D. L. (1992) *FASEB J.* 6, 2684-2690]. The action of the toxin and cells were then evaluated by measuring an immune response to the tumor cells: irradiated tumor cells were injected into one ear, and the response was determined by measuring the swelling of the ear. When administered with irradiated cells, the addition of toxin-treated cells increased swelling whereas the addition of toxin-treated cells lysed by freeze thawing did not. Similarly, in this experiment, vaccination with irradiated cells alone was not sufficient: the addition of pertussis toxin or intact toxin-treated cells was required. The conclusion is thus that 3CX4 blocks the action of pertussis toxin bound to the membranes of spleen cells.

Recently, a report [Dranoff et al., 1993, supra] demonstrated protection of mice from B-16 melanoma using irradiated cells transfected with DNA causing production of GM-CSF. This report also examined the protocols used in previous studies of protection which employed tumor cells transfected to produce other cytokines. The examination suggested that the lack of a critical control in these other studies created the misleading impression that these cytokines were crucial for the protective effect. The control omitted in these previous studies was vaccination with irradiated cells alone. Several of the examples reported herein include this control, further confirming the utility of the compositions and methods of the present invention.

The invention may be better understood with reference to the accompanying examples, which are intended for purposes of illustration only and should not be construed as in any sense limiting the scope of the present invention as defined in the claims appended hereto.

EXAMPLES

In the following examples, pertussis toxin was obtained from either List Laboratories or the State of Michigan Department of Public Health. The recombinant, inactive analog of pertussis toxin contained inactivating mutations in the S1 subunit (arg7->lys and glu129->gly) [Nencioni et al., 1990, supra]. Mice were obtained from standard commercial sources. The hybridoma producing monoclonal antibody 3CX4 [Kenimer et al., 1989, supra] was a gift from Dr. James Kenimer; the antibody was purified from ascites fluid using a protein A affinity procedure (Pierce Biochemical Co.) The amounts of pertussis toxin and antibody are stated in terms of grams of protein determined by colorimetric protein assay [Lowry, O. H., Rosebrough, N. J., Farr, A. L., & Randall, R. J. (1951) *J. Biol. Chem.* 193, 265-275; Bensadoun, A., & Weinstein, D. (1976) *Anal. Biochem.* 70, 241-250].

The B16 melanoma cell line was studied using syngeneic C57BL/6 mice and was obtained from Dr. Malcolm Mitchell [Staib, L., Harel, W., & Mitchell, M. S. (1993) *Can. Res.* 53, 1113-1121]. The line 1 carcinoma and the subline producing ovalbumin were studied using syngeneic BALB/c mice and were a gift from Dr. John Frelinger [Blieden, et al., 1991, supra]. The cells were cultured and released from dishes as described [Blieden, et al., 1991, supra; Staib et al., 1993, supra], collected by centrifugation, and resuspended in serum-free media prior to irradiation and/or injection.

Vaccinations were performed by administering, as separate intraperitoneal injections, either vehicle or an antigen preparation consisting of irradiated tumor cells, and/or pertussis toxin (400 ng per mouse) or carrier as shown in the examples. Either before or after these vaccinations, the mice were challenged with live tumor cells via a subcutaneous injection in the upper back.

Examples 1-3 demonstrate that pertussis toxin enhances anti-tumor responses against B16 melanoma.

Example 1 (MLT2)

On Day 0, 100,000 B16 cells were injected subcutaneously (SQ) in the back. On Day 17, mice were given intraperitoneal (ip) injections consisting of various combinations of phosphate-buffered saline (PBS), 400 ng of pertussis toxin (PT) or recombinant, transferase-deficient pertussis toxin (rPT), and/or 300,000 irradiated B16 melanoma cells (ir-B16). On Days 26 and 38 a second and third set of ip injections were given. On Day 153, all surviving mice were challenged (SQ) with 100,000 B16 cells. On Day 259, all surviving mice were again challenged (SQ) with 100,000 B16 cells. In this example, the B16 cells were cultured with gamma-interferon for 24-48 hours prior to injection.

Mice were examined for physical evidence of tumor bulging outward from the back or side, and the length of the tumor was recorded to the nearest cm. Typically death occurred when tumors were greater than 2 cm in length. Death was associated with clearly-evident tumor growth. Other data suggested that, at times, there can be incomplete tumor take in control animals. Thus, to better demonstrate generation of an anti-tumor response, survivors were subjected to the subsequent tumor challenges on Days 153 and 259.

The data for this example are summarized in Table 1 (MLT2). Pertussis toxin stimulated an anti-tumor response.

Example 2

The data for this example are shown in FIG. 1 and show pertussis toxin stimulated an anti-tumor response. Ten days prior to tumor challenge (Day-10), six groups each containing six mice were injected intraperitoneally (ip) with different combinations of antigen (300,000 irradiated B16 cells previously treated with interferon-gamma, B16-IFNg(0.3) and 400 ng pertussis toxin (PT, from two different lots termed 48A and 55A). On Day 0, the mice were all challenged with 100,000 B16 cells not treated with gamma-interferon injected subcutaneously into the back, just below the neck. Tumor size was scored and the date of death recorded.

Example 3

The data for this example are shown in FIG. 2 and show that pertussis toxin stimulated an anti-tumor response. Ten days prior to tumor challenge (Day-10), eight groups of six mice were injected, some with 400 ng pertussis toxin (PT), and some with different antigen preparations: irradiated B16 cells (B16) either with or without a prior treatment with interferon-gamma (IFNg), either fresh (no notation) or frozen (frzn), and either 300,000 (0.3) or 2,000,000 (2.0) cells. On Day 0, all the mice were challenged with an SQ injection in the back of 100,000 B16 cells. Tumor size was scored and the date of death recorded. A second set of mice were vaccinated as shown in the figure below, but the vaccinations were 4 days after initiation of tumor. None of these mice were protected from the tumor.

Examples 4 and 5 demonstrate that pertussis toxin enhances anti-tumor responses against line 1 lung carcinoma.

Example 4

The data for this example are shown in FIG. 3 and show that pertussis toxin stimulated an anti-tumor response against line 1 tumor cells. Fifteen days prior to challenging mice with an SQ injection of 50,000 line 1 tumor cells, 12 mice were divided into two groups each containing six mice. Both groups were injected (ip) with 300,000 irradiated line 1 tumor cells. One group received in addition an ip injection of 400 ng pertussis toxin. The mice were observed for tumor growth and the date of death recorded.

Example 5

The data for this example are shown in FIG. 4 and show that pertussis toxin stimulated an anti-tumor response. Twelve days prior to challenging mice with an SQ injection of 50,000 line 1 tumor cells transfected with DNA encoding ovalbumin (L1-Ova), 18 mice were divided into three groups each containing six mice. One group was injected (ip) with 300,000 irradiated L1-Ova tumor cells. One group received 300,000 irradiated cells and an additional ip injection of 400 ng pertussis toxin. One group received neither cells nor toxin. The mice were observed for tumor growth and the date of death recorded.

Examples 6-8 establish that treating spleen cells with pertussis toxin is sufficient to enhance anti-tumor effects.

Example 6

The data for this example show that the monoclonal antibody termed 3CX4 blocks pertussis toxin action in vivo. The assay involved measuring a delayed-type hypersensitivity (DTH) response to irradiated L1-Ova tumor cells injected into the ear of a mouse. The DTH response is seen as a swelling of the ear over a period of several days. In this example, the swelling is expressed as the difference in thickness between the ear injected with tumor cells, and the other ear which was injected with a solution containing ovalbumin.

Nine days prior to injection of irradiated L1-Ova cells into the ear, groups of six mice were injected ip with combinations of 300,000 irradiated L1-Ova cells, 400 ng pertussis toxin, or spleen cells from other, naive BALB/c mice. The spleen cells were first incubated overnight in RPMI tissue culture media supplemented with 10% fetal bovine serum. To some of the cultured cells was added 400 ng pertussis toxin per $10^8$ spleen cells prior to the overnight incubation. The next day, the cells were centrifuged, the culture media removed, and fresh media added. The anti-pertussis toxin monoclonal antibody termed 3CX4 [Kenimer et al., 1989, supra] was then added to some of the cells (1 mg added per $10^8$ cells); some of the cells were also lysed by freeze thawing.

Mice were then injected, ip, with 300,000 irradiated L1-Ova cells. The mice were divided into six groups of six mice each. The groups received additional ip injections of either vehicle, 400 ng pertussis toxin (PT-direct), or the spleen cells incubated either with or without pertussis toxin and 3CX4. One set of mice received spleen cells that were incubated with pertussis toxin followed by 3CX4 and then were lysed by freeze-thawing (spl. cells +PT +3CX4->FT). For clarity, the data showing the effect of freeze-thawing are extracted out of the first panel and shown in a second panel. The data clearly show that the effect of PT was blocked by freeze-thawing the spleen cells. Thus, the effect of pertussis toxin can be mediated by spleen cells altered by the toxin in culture, it is not required to intoxicate cells of the recipient mouse.

Example 7

Figure 6:
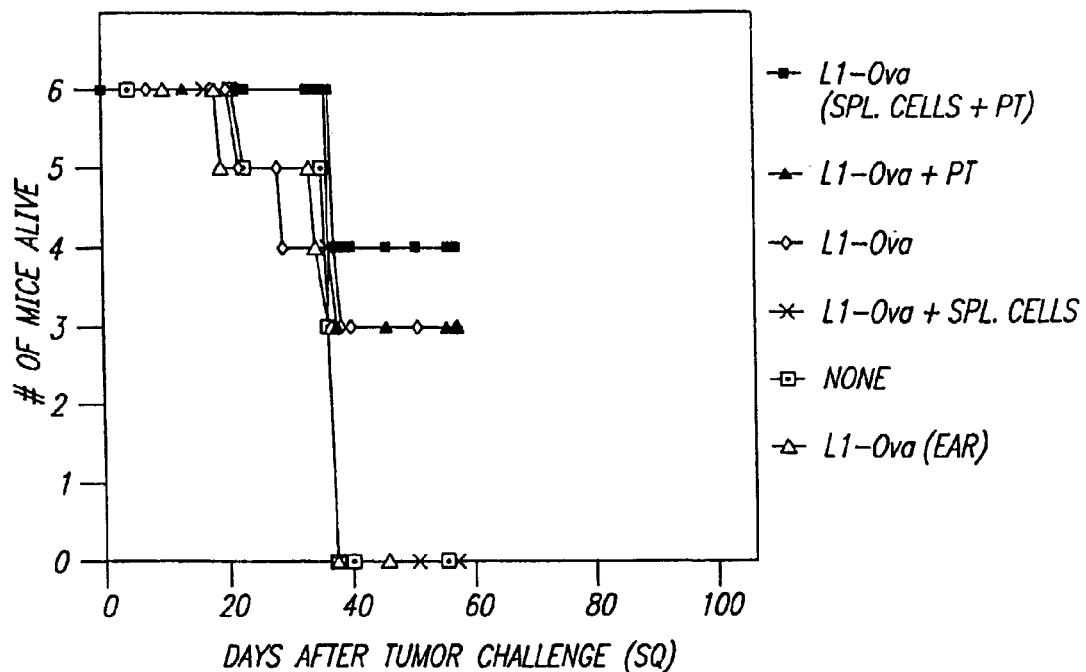
FIG. 6 illustrates the protection against L1-Ova cells afforded by a vaccination of BALB/C mice with irradiated L1-Ova cells with or without the conadministration of pertussis toxin, or spleen cells incubated with or without pertussis toxin and mixed with 3CX4.

The data for this example are shown in FIG. 6 and show that spleen cells incubated with pertussis toxin stimulate an anti-tumor response against L1-Ova tumor cells. Thirteen days prior to challenging mice with an SQ injection of 50,000 L1-Ova cells, mice were divided into groups containing six mice, and injected ip with either antigen (300,000 irradiated L1-Ova tumor cells) and/or adjuvant. The adjuvant was either 400 ng pertussis toxin, or spleen cells cultured overnight with or without pertussis toxin, washed, and then mixed with 3CX4 as described in Example 6. On Day 0, the mice were challenged with tumor cells; one group received a dose of irradiated cells in the ear as described in Example 6. The mice were evaluated for tumor growth and the date of death noted.

Example 8

Figure 7:
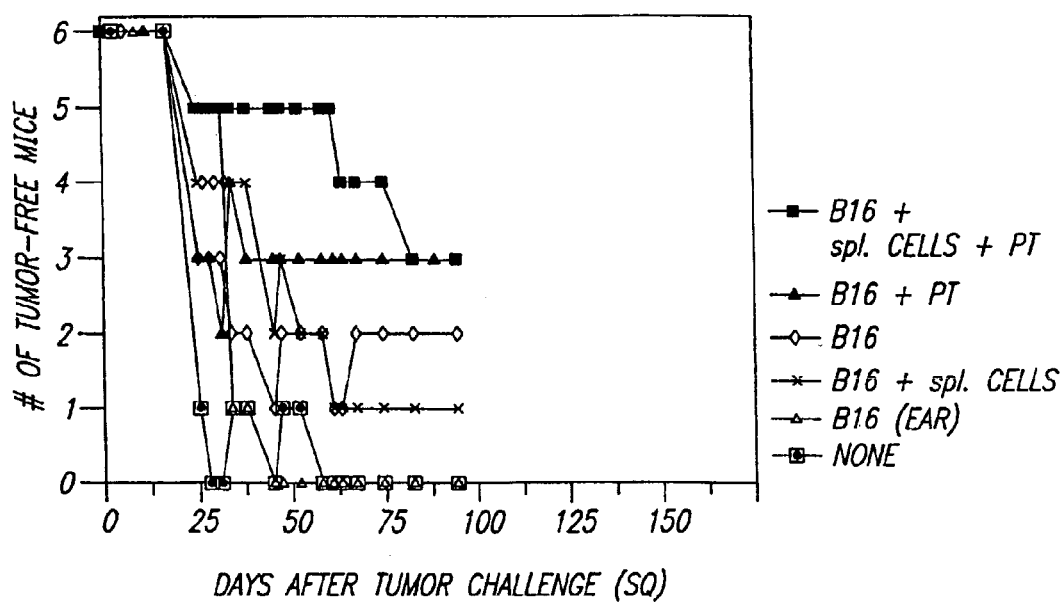
FIG. 7 illustrates the protection against B16 melanoma afforded by vaccination of C57/BL mice with irradiated B16 cells with or without the coadministration of pertussis toxin, or spleen cells incubated either with or without pertussis toxin and then mixed with 3CX4.

The data for this example are shown in FIG. 7 and show that spleen cells incubated with pertussis toxin stimulate an anti-tumor response against B16 tumor cells. Fourteen days prior to challenging mice with an SQ injection of 300,000 B16 tumor cells, mice were divided into groups containing six mice, and injected ip with either antigen (300,000 irradiated B16 tumor cells) and/or adjuvant. The adjuvant was either 400 ng pertussis toxin, or spleen cells cultured overnight with or without pertussis toxin, washed, and then mixed with 3CX4 as described in Example 6. On Day 0, the mice were challenged with tumor cells; one group received a dose of irradiated cells in the ear as described in Example 6. The mice were visually inspected for evidence of tumor growth. Those with no evidence of tumor growth were termed "tumor-free." In this example, some tumors regressed and then reappeared.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and any specific terms employed herein are intended in a descriptive sense and not for purposes of limitation.

What is claimed is:

1. A method for promoting an anti-tumor response directed against a target tumor-related antigen in a mammalian patient, said method comprising administering to the patient:

an effective amount of composition comprising at least one active agent, wherein the active agent is selected from the group consisting of isolated pertussis toxin and analogs thereof exhibiting ADP-ribosyltransferase activity, said agent capable of eliciting an immune response against a tumor in a patient having a tumor or previously afflicted with a tumor, a suitable carrier or excipient, and a target tumor related antigen selected from the group consisting of tumor cells, irradiated cells, and tumor associated antigens.

2. A method according to claim 1, wherein the patient has been previously afflicted with a tumor, and wherein the anti-tumor response is prophylactic.

3. A method according to claim 1, wherein the anti-tumor response is therapeutic.

4. A method for promoting an anti-tumor response directed against a tumor-related antigen that is present in a mammalian patient, said method comprising:

administering to the patient:

an amount of a composition comprising at least one active agent, wherein the active agent is selected from the group consisting of isolated pertussis toxin and analogs thereof exhibiting ADP-ribosyltransferase activity, wherein said analog comprises the S1 subunit of pertussis toxin and effective to promote an immune response against a tumor in a patient having a rumor or previously afflicted with a tumor; and a suitable carrier or excipient.

5. A method according to claim 4, wherein the patient has been previously afflicted with a tumor, and wherein the anti-tumor response is prophylactic.

6. A method according to claim 4, wherein the anti-tumor response promoted is therapeutic.

7. A method according to claim 1, wherein the target antigen is administered prior to, during or after administration of the composition.

* * * * *